(12) United States Patent
Kiani (10) Patent No.: US 9,326,712 B1
(45) Date of Patent: May 3, 2016

(54) OPTICOUSTIC SENSOR

(75) Inventor: Massi Joe E. Kiani, Laguna Niguel, CA (US)

(73) Assignee: Masimo Corporation, Irvine, CA (US)

(*) Notice: Subject to any disclaimer, the term of this patent is extended or adjusted under 35 U.S.C. 154(b) by 1312 days.

(21) Appl. No.: 13/152,259

(22) Filed: Jun. 2, 2011

Related U.S. Application Data (60) Provisional application No. 61/350,673, filed on Jun. 2, 2010.

(51) Int. Cl.
| | | |
|---|---|---|
| *A61B 5/1455* | (2006.01) | |
| *A61B 8/02* | (2006.01) | |
| *A61B 8/06* | (2006.01) | |
| *A61B 5/00* | (2006.01) | |
| *A61B 5/0205* | (2006.01) | |
| *A61B 5/08* | (2006.01) | |

(52) U.S. Cl.
CPC ............ *A61B 5/1455* (2013.01); *A61B 5/0205* (2013.01); *A61B 5/0816* (2013.01); *A61B 5/6822* (2013.01); *A61B 5/6832* (2013.01); *A61B 8/06* (2013.01)

(58) Field of Classification Search
CPC ............ A61B 5/1455; A61B 5/14551; A61B 5/14552; A61B 5/7435; A61B 5/6823; A61B 5/6832; A61B 5/7475; A61B 5/029; A61B 5/0205; A61B 5/6814; A61B 5/6822; A61B 5/0816; A61B 8/00; A61B 8/06
USPC .................. 600/310, 323, 324, 344, 437, 459
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |

(Continued)

OTHER PUBLICATIONS

Eldor et al., "A device for monitoring ventilation during anaesthesia; the paratracheal audible respiratory monitor", Canadian Journal of Anaesthesia, 1990, vol. 9, No. 1, p. 95-98.

*Primary Examiner* — Eric Winakur
(74) *Attorney, Agent, or Firm* — Knobbe Martens Olson & Bear LLP (57) ABSTRACT

A physiological sensor has an optic assembly, an acoustic assembly and an attachment assembly. The optic assembly has an optic transducer that is activated so as to transmit a plurality of wavelengths of light into a tissue site and to detect the light after attenuation by pulsatile blood flow within the tissue site. The acoustic assembly has an acoustic transducer activated so as to respond to vibrations at the surface of the tissue site. The attachment assembly affixes the optic assembly and acoustic assembly to the tissue site, such as along one side of a person's neck or the forehead. A sensor cable extends from the attachment assembly so as to transmit an optic transducer signal and an acoustic transducer signal to a monitor for calculation of physiological parameters.

6 Claims, 11 Drawing Sheets

(56) References Cited

U.S. PATENT DOCUMENTS

| | | |
|---|---|---|
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,977,538 A * | 11/1999 | Unger et al. .................. 600/310 |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |

(56) References Cited

U.S. PATENT DOCUMENTS

| | | | |
|---|---|---|---|
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,430,817 B1 * | 4/2013 | Al-Ali et al. ................ 600/323 |
| 8,517,981 B2 * | 8/2013 | Zornow ................ 600/323 |
| 2008/0077026 A1 * | 3/2008 | Banet et al. ................ 600/509 |

* cited by examiner

OPTICOUSTIC SENSOR

PRIORITY CLAIM TO RELATED PROVISIONAL APPLICATIONS

The present application claims priority benefit under 35 U.S.C. §119(e) to U.S. Provisional Patent Application Ser. No. 61/350,673 filed Jun. 2, 2010, titled Opticoustic Sensor; the above-cited provisional patent application is hereby incorporated by reference herein.

BACKGROUND OF THE INVENTION

Various sensors may be applied to a person for measuring physiological parameters indicative of health or wellness. As one example, a pulse oximetry sensor generates a blood-volume plethysmograph waveform from which oxygen saturation of arterial blood and pulse rate may be determined, among other parameters. As another example, an acoustic sensor may be used to detect airflow sounds in the lungs, bronchia or trachea, which are indicative of respiration rate.

SUMMARY OF THE INVENTION

An optical-acoustic ("opticoustic") sensor integrates an optic sensor for measuring blood flow parameters with an acoustic sensor for measuring body-sound parameters. Such integration increases the number of important physiological parameters available from a single sensor site or proximate sensor sites. Further, such integration allows improved measurements of physiological parameters.

In an advantageous embodiment, an opticoustic sensor applied to a neck site utilizes a piezo element to measure respiration rate acoustically (RRa), such as from trachea airflow sounds, and LEDs to measure respiration rate optically (RRo) from pulsatile blood flow. Such opticoustic-derived respiration rate (Roa) based upon both RRa and RRo provides a more accurate or more robust measure of respiration rate RR than achievable from either acoustic or optical sensors alone.

In an advantageous embodiment, a tissue-profile opticoustic sensor has an array of optical elements for distinguishing tissue depth. Applied to a neck site, the opticoustic sensor provides RRoa, as described above, in addition to measurements of carotid oxygen saturation ($SpO_2$) and jugular (pulsatile) vein $SpO_2$ along with peripheral tissue $SpO_2$. The difference between carotid artery and jugular vein $SpO_2$ advantageously allows an indirect measure of brain oximetry parameters including brain oxygen demand and metabolism.

In an advantageous embodiment, a tissue-profile opticoustic sensor applied to a forehead site advantageously provides respiration parameters based upon paranasal sinus ostium airflow, turbulence and echoes and, further, cerebral oxygen saturation based upon pulsatile flow in blood-perfused brain tissues at various depths. Attached to a back or chest site, a tissue profile opticoustic sensor provides respiration parameters based upon turbulent airflow in the lungs and various airways along with neonatal core oxygen saturation.

Problems also arise when multiple sensors are used simultaneously for patient monitoring. Each sensor utilizes its own cable and connector, and multiple sets of cables applied to different patient sites tend to tangle and rub together. This can cause electrical and acoustic noise, which affect the sensors and lead to inaccurate readings for measured parameters. Further, a patient tethered to a variety of cumbersome cables and connectors that limit patient movement may experience discomfort. In addition, it is inconvenient and time consuming for a caregiver to repeatedly connect and disconnect multiple cable sets between sensors and monitors.

In an advantageous embodiment, an integrated opticoustic sensor provides respiration rate based upon trachea airflow sounds and oxygen saturation and pulse rate based upon pulsatile blood flow within perfused ear tissues. In particular, proximate neck and ear site attachment embodiments measure oxygen saturation, pulse rate and respiration rate among other blood parameters. In addition, these major vital sign measurements can be taken with the attachment-detachment ease and convenience of a single sensor and with minimal patient discomfort.

DETAILED DESCRIPTION OF THE PREFERRED EMBODIMENTS

Figure 1A:
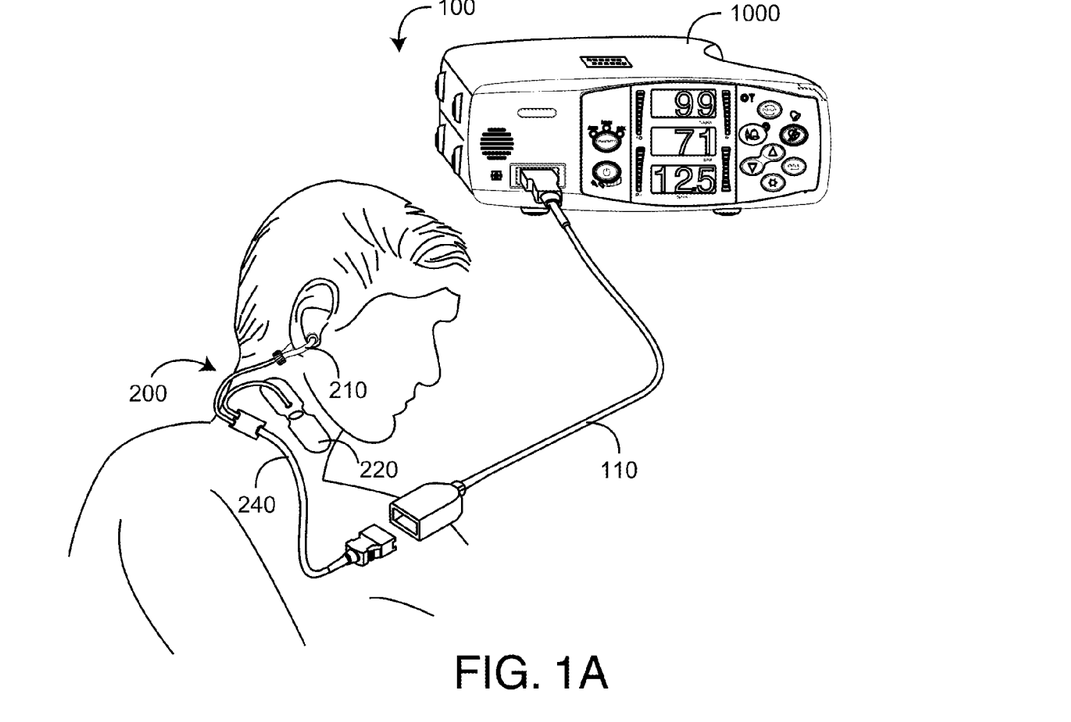
FIGS. 1A-B are illustrations of optical-acoustic ("opticoustic") sensor embodiments in communications with an opticoustic monitoring platform.
Figure 1B:
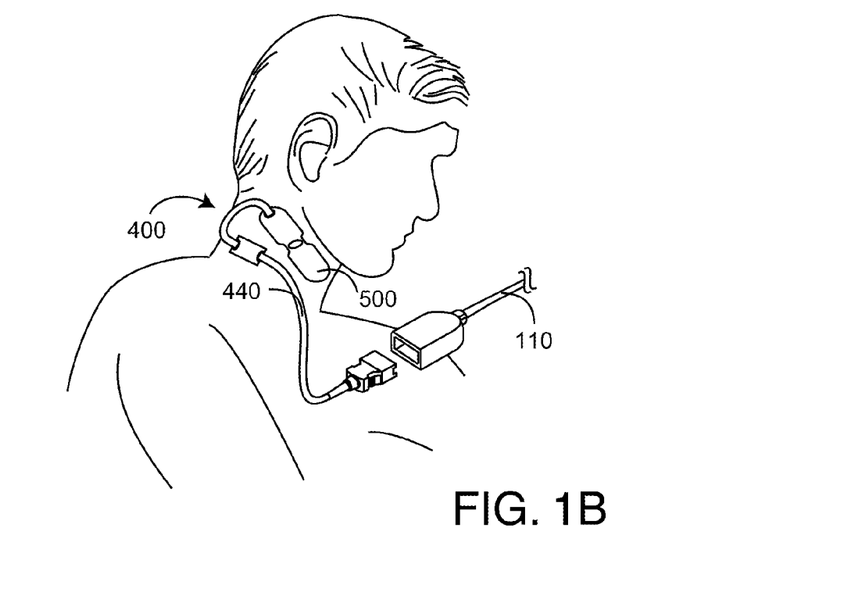

FIGS. 1A-B illustrate a patient monitoring system 100 having a monitor 1000 in communications with optical-acoustic ("opticoustic") sensor embodiments 200, 400. As shown in FIG. 1A, an opticoustic sensor 200 attaches to a neck site so as to detect tracheal airflow sounds and an proximate ear site on a person so as to detect optical changes due to pulsatile flow in blood-perfused concha tissues, as described in detail with respect to FIGS. 2-3, below. An integrated sensor cable 240 links the sensor 200 to a patient cable 110, and the patient cable 110 links the sensor cable 240 to the monitor 1000, allowing communications between the sensor 200 and monitor 1000, as described in detail with respect to FIG. 9A, below. The monitor 1000 processes the opticoustic sensor signals so as to calculate optically-derived blood parameters from the optic head 210, such as pulse rate (PR) and oxygen saturation ($SpO_2$), to name a few, and acoustically-derived parameters from the acoustic head 220, such as respiration rate (RR), as described in detail with respect to FIG. 10, below.

As shown in FIG. 1B, in another embodiment, an opticoustic sensor 400 attaches to a single tissue site, such as a neck, forehead, chest or back, to name a few, so as to generate acoustic-based and optic-based sensor signals, as described in detail with respect to FIGS. 4-5, below. An integrated sensor cable 440 links the sensor 400 to a monitor 1000 (FIG. 1A) via a patient cable 110 (FIG. 1A), as described in detail with respect to FIG. 9B, below. The monitor 1000 processes the opticoustic sensor signals so as to calculate acoustically-derived and optically-derived parameters from the integrated opticoustic sensor head 500, as described in detail with respect to FIG. 10, below.

In an advantageous embodiment, an opticoustic sensor 200 (FIG. 1A), 400 (FIG. 1B) utilizes a piezo element to measure respiration rate acoustically (RRa), such as from trachea airflow sounds, and LEDs to measure respiration rate optically (RRo) from pulsatile blood flow. Such opticoustic-derived respiration rate (Roa) based upon both RRa and RRo provides a more accurate or more robust measure of respiration rate RR than achievable from either acoustic or optical sensors alone. Optically-derived respiration rate RRo is described in U.S. patent application Ser. No. 13/076,423 titled Plethysmographic Respiration Processor filed Mar. 30, 2011, assigned to Masimo Corporation, Irvine, Calif. ("Masimo") and incorporated by reference herein.

Although capable of simultaneous optic and acoustic measurements at a single site, the opticoustic sensor 400 may also be advantageously used for optic measurements at one site and acoustic measurements at another site. For example, respiration rate may be monitored with the sensor head 500 attached to a neck site and cerebral oximetry may be monitored with the sensor head 500 attached to a forehead site.

Although described above with respect to respiration rate measurements, an opticoustic sensor 200, 400 may provide acoustic-based parameters based upon any of various body sounds monitored at a variety of tissue sites, with applications ranging from cardiac function analysis and diagnosis to acoustic rhinometry. Likewise, optic-based parameters may be based on blood flow monitored at a variety of tissue sites.

Figure 2:
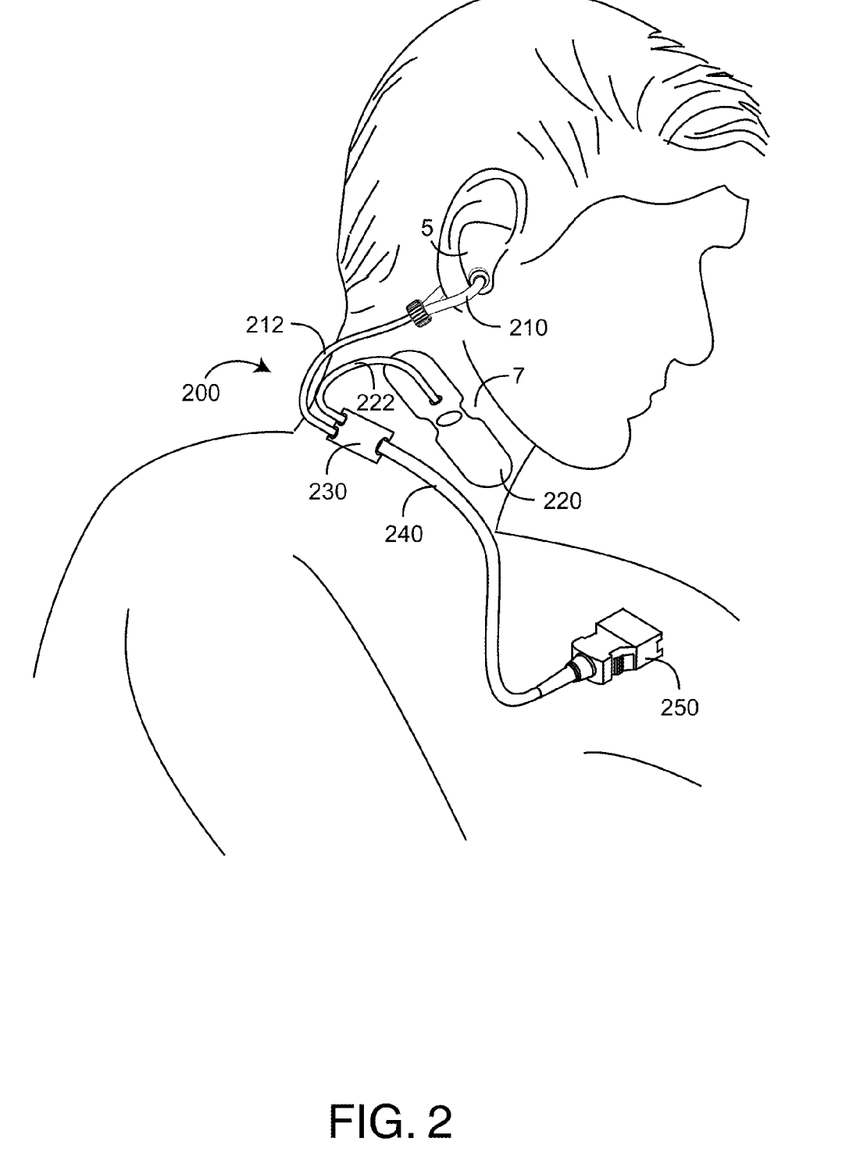
FIG. 2 is an illustration of an opticoustic sensor embodiment for measurements of acoustically-derived parameters at a neck site and optically-derived parameters at a proximate ear site.

FIG. 2 illustrates an opticoustic sensor embodiment 200 providing respiration rate based upon trachea airflow sounds in addition to oxygen saturation and pulse rate measurements based upon pulsatile blood flow in ear tissues. The opticoustic sensor 200 has an acoustic head 220 configured for a neck site 7 and an optic head 210 configured for an ear concha site 5 proximate to the neck site 7, i.e. on the same side of the head as the neck site 7. Advantageously, the proximate ear site 5 and neck site 7 allows the sensor to be applied and removed with the ease and convenience of a single site sensor. An optic head cable 212 interconnects the optic head 210 to a sensor cable 240. An acoustic head cable 222 interconnects the acoustic head 220 to the sensor cable 240. An anchor 230 attaches to the patient's neck so as to stabilize the cables 212, 222, 240 and prevent rubbing and movement that might generate mechanical and/or electrical noise, which interferes with the sensor signal. Advantageously, the two sensor heads 210, 220 provide complementary physiological measurements, with the acoustic head 220 providing respiration rate based upon trachea airflow sounds and the optic head 210 providing oxygen saturation and pulse rate measurements, among others, based upon pulsatile blood flow in perfused ear (concha) tissues. The sensor cable 240 communicates between the opticoustic sensor 200 and a patient monitor 1000 (FIG. 1A) via a sensor cable connector 250. The opticoustic sensor output can be processed by a single monitoring platform sharing common signal processing hardware, as described with respect to FIG. 10, below.

As shown in FIG. 2, one embodiment of the optic head 210 is a "Y"-clip having a base, a pair of curved clips extending from the base, an emitter assembly extending from one clip end and a detector assembly extending from another clip end. The clips are tubular so as to accommodate wires from the emitter/detector assemblies, which extend from apertures in the base. Each assembly has a pad, a molded lens and a lid, which accommodate either an emitter subassembly or a detector subassembly. The Y-clip flexes so as to slide over the ear periphery and onto either side of the concha. The Y-clip, so placed, can transmit multiple wavelength light into the concha tissue and detect that light after attenuation by pulsatile blood flow within the concha tissue. Ear sensor embodiments are described in U.S. patent application Ser. No. 12/706,711, titled Ear Sensor, filed Feb. 16, 2010, assigned to Masimo and incorporated by reference herein.

In an embodiment, the Y-clip emitter includes both a red light emitting diode (LED) and an infrared (IR) LED. The detector is a photodiode that responds to both the red and infrared emitted light so as to generate an output signal to the monitor. The LEDs emit light into the ear concha. The photodiode is positioned opposite the emitters so as to detect the LED emitted light after attenuation by the blood-perfused concha tissue. The emitter and detector have pinouts to the connector 250, which provides sensor communication with the monitor. The monitor determines oxygen saturation by computing the differential absorption by arterial blood of the two wavelengths of emitted light, as is well-known in the art. Although described above with respect to a Y-clip attached to an ear concha site, the optic head 210 may comprise any of a variety of transmission-mode or reflectance-mode sensors attached to various ear tissue sites, such as an ear lobe or an ear canal, as described in U.S. patent application Ser. No. 12/706,711, cited above.

Also shown in FIG. 2, one embodiment of the acoustic head 220 is an attachment assembly configured to hold a sensor assembly in contact with a neck site 7. The attachment assembly has lateral extensions symmetrically placed about a sensor assembly, which has a piezoelectric membrane mounted in a support frame. The piezoelectric membrane moves on the frame in response to acoustic vibrations, thereby generating electrical signals indicative of the bodily sounds of the patient. An acoustic coupler generally envelops the other sensor elements and improves the coupling between the neck skin and the piezoelectric membrane. Acoustic sensor embodiments, including embodiments of attachment subassemblies and piezoelectric transducer subassemblies thereof, are described in U.S. patent application Ser. No. 12/643,939 titled Acoustic Sensor Assembly, filed Dec. 21, 2009 and U.S. patent application Ser. No. 12/904,789 titled Acoustic Respiratory Monitoring Systems and Methods, filed Oct. 14, 2010, both patent applications assigned to Masimo and both incorporated by reference herein.

Figure 3A:
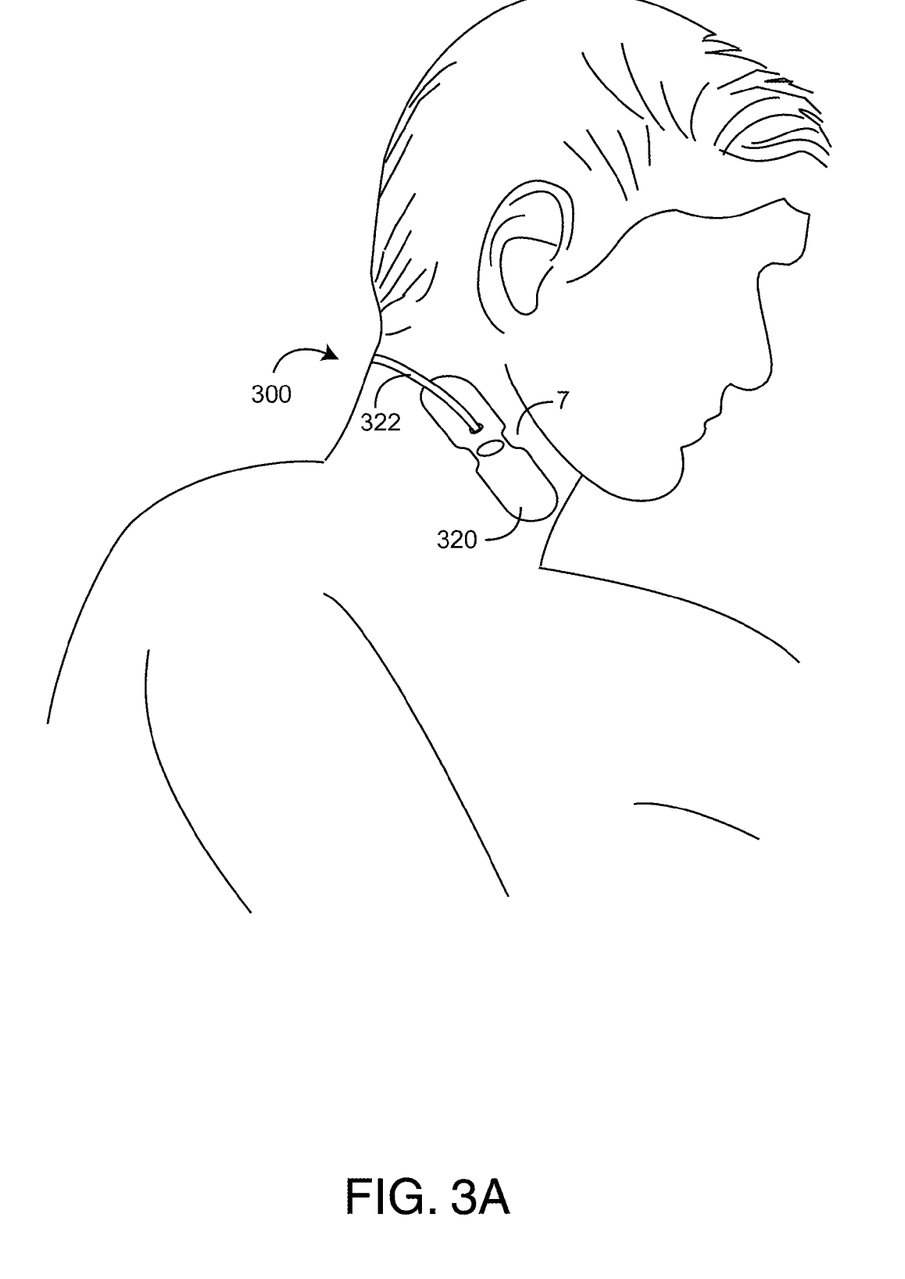
FIGS. 3A-B are illustrations of an opticoustic sensor embodiment for measuring acoustically-derived parameters at a neck site and optically-derived parameters at a distal ear site.
Figure 3B:
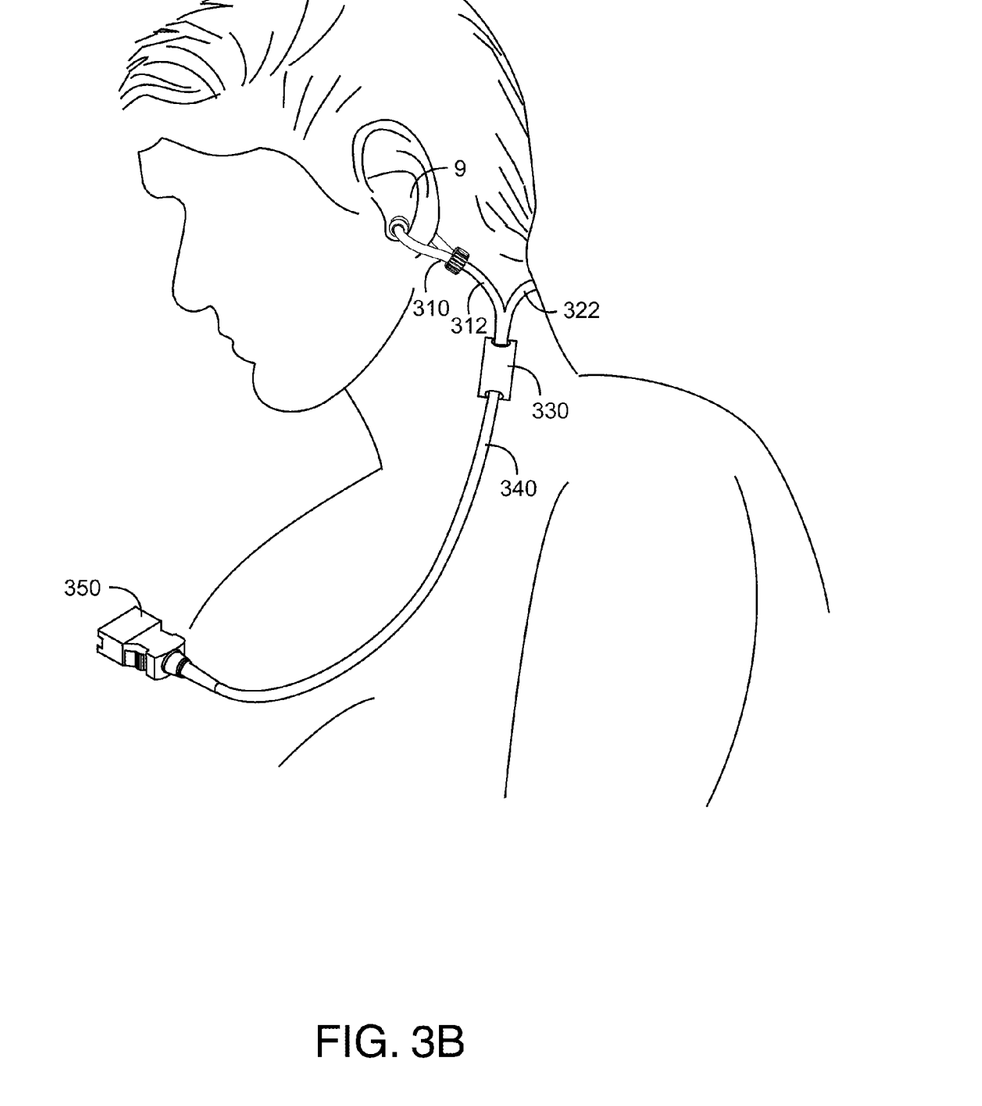

FIGS. 3A-B illustrate an opticoustic sensor embodiment 300 providing respiration rate based upon trachea airflow sounds in addition to oxygen saturation and pulse rate measurements based upon pulsatile blood flow in ear tissues. The opticoustic sensor 300 has an acoustic head 320 configured for a neck site 7 (FIG. 3A) and an optic head 310 configured for an ear concha site 9 (FIG. 3B) distal to the neck site 7 (FIG. 3A), i.e. on the opposite side of the head. The opticoustic sensor 300 has an optic head 310 configured for an ear concha site 9 and an acoustic head 320 configured for a neck site 7. Advantageously, the neck site 7 and distal ear site 9 removes the optic head cable 312 and the sensor cable 340 from proximity to the acoustic head 320, eliminating any potential for movement of these cables 312, 340 from creating acoustic noise that could interfere with the acoustic head 320. An optic head cable 312 interconnects the optic head 310 to a sensor cable 340. An acoustic head cable 322 routes behind a patient neck so as to interconnect the acoustic head 320 to the sensor cable 340. An anchor 330 attaches to the patient's neck so as to stabilize the optical and acoustic head cables 312, 322 and the interconnecting sensor cable 340. The sensor cable 340 communicates between the opticoustic sensor 300 and a patient monitor 1000 (FIG. 1A) via a sensor cable connector 350. The opticoustic sensor output can be processed by a single monitoring platform sharing common signal processing hardware, as described with respect to FIG. 10, below.

Figure 4A:
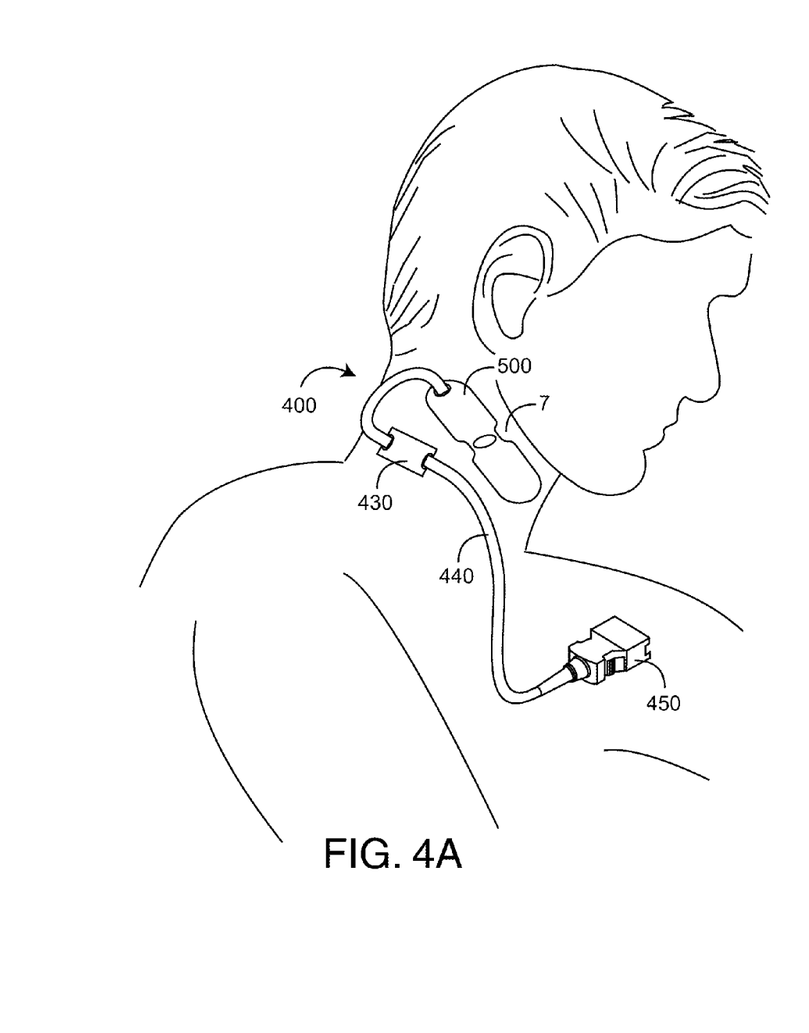
FIGS. 4A-B are illustrations of an opticoustic sensor embodiment for measuring acoustically-derived parameters and optically-derived parameters at a single tissue site, such as a neck or forehead.
Figure 4B:
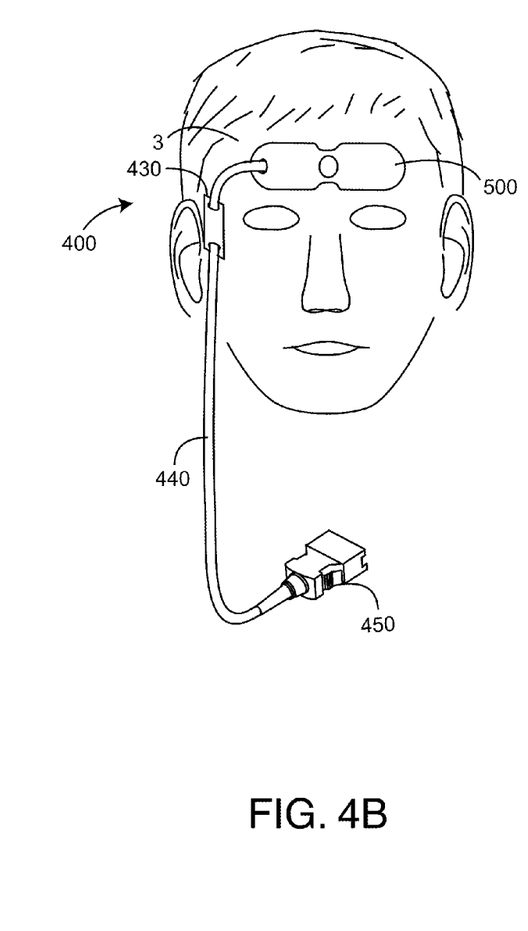

FIGS. 4A-B illustrate an opticoustic sensor embodiment 400 providing respiration-related parameters based upon airflow sounds in addition to pulsatile blood flow-related parameters, such as pulse rate and oxygen saturation. The opticoustic sensor 400 has a sensor head 500, a sensor cable 440, a cable anchor 430 and a sensor cable connector 450. The sensor head 500 advantageously integrates both an optic assembly and an acoustic assembly into an integrated adhesive media that can be quickly and easily applied to a neck site 7 or a forehead site 3, to name a few, so as to measure a wide range of physiological parameters. The sensor cable 440 communicates sensor signals and monitor control signals between the sensor head 500 and the sensor connector 450. The sensor connector 450 mates with a patient cable 110 (FIG. 1A) or directly with a patient monitor 1000 (FIG. 1A). The optic and acoustic assemblies are described in further detail with respect to FIGS. 5-6, below.

Figure 5A:
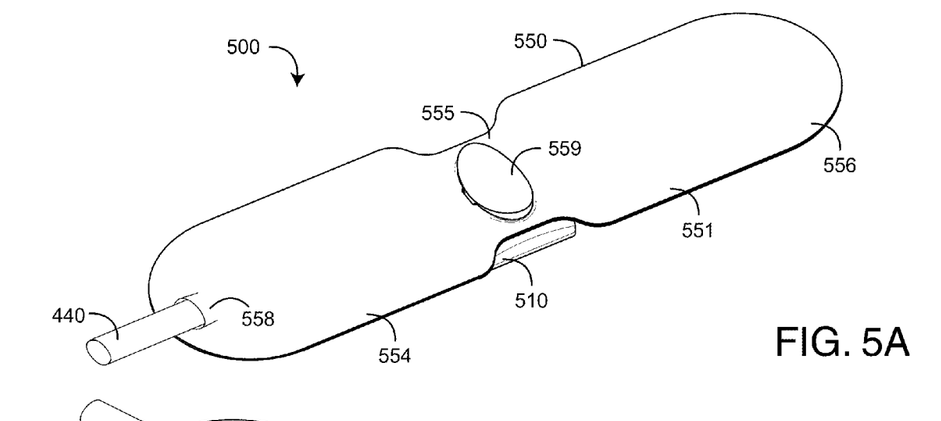
FIGS. 5A-B are detailed top and bottom perspective views, respectively, of an opticoustic sensor head.
Figure 5B:
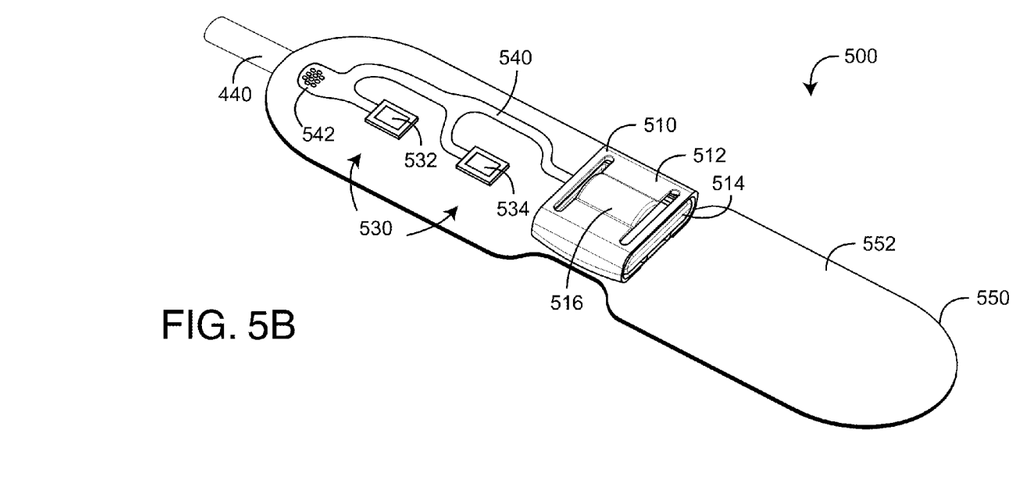

FIGS. 5A-B illustrates a sensor head 500 for an opticoustic sensor embodiment 400 (FIGS. 4A-B). The sensor head 500 has acoustic 510, optic 530, interconnect 540 and attachment 550 assemblies. The acoustic assembly 510 has an acoustic coupler 512 and a piezoelectric subassembly 514. The acoustic coupler 512 generally envelops or at least partially covers some or all of the piezoelectric subassembly 512. The piezoelectric subassembly 512 includes a piezoelectric element and a support frame (not visible). The piezoelectric membrane is configured to move on the frame in response to acoustic vibrations, thereby generating electrical signals indicative of the bodily sounds of the patient. The acoustic coupler 512 advantageously improves the coupling between the acoustic signal measured at the patient's skin and the piezoelectric element. The acoustic coupler 512 includes a contact portion 516, which is brought into contact with the skin of the patient. As an example, at a neck site the acoustic assembly is responsive to tracheal air flow sounds that can yield a patient's respiration rate.

As shown in FIG. 5B, the optic assembly 530 has an emitter subassembly 532 and a detector subassembly 534. The emitter subassembly 532 includes multiple light emitting diodes and/or laser diodes (collectively "LEDs") that emit narrow bandwidth light centered on at least two discrete wavelengths in the red and IR spectrums. The LEDs may be mounted on the attachment assembly 550 or mounted remotely, such in the sensor cable connector 450 (FIGS. 4A-B) or the monitor 1000 (FIG. 1A). If mounted remotely, light output from the LEDs may be transported via optical fibers to the emitter subassembly 532. The detector subassembly 534 includes at least one photodiode detector and has a response bandwidth that includes all of the emitter subassembly 532 bandwidths. In an embodiment, the emitter subassembly 532 includes an addressable, monolithic LED array that is mechanically mounted and electrically interconnected in an encapsulated cavity of a ceramic substrate. In an embodiment, the detector subassembly 534 includes a monolithic Si photodiode or a combination of a monolithic Si photodiode and a monolithic InGaAs photodiode mechanically mounted and electrically interconnected in an encapsulated and electromagnetically shielded cavity of a ceramic substrate. The optical assembly 530 is configured so that light transmitted from the emitter 532 passes into patient tissue and is reflected back to the detector 534 after attenuation by pulsatile blood flow in the tissue.

Further shown in FIG. 5B, the acoustic assembly 510 and optic assembly 530 communicate with the sensor cable 440 via the interconnect assembly 540. In an embodiment, the interconnect assembly 540 is a flex circuit having multiple conductors that is adhesively bonded to the attachment assembly 550. The interconnect assembly 540 has a solder pad 542 or other interconnect to interface with the sensor cable 440, and the attachment assembly 550 has a molded strain relief 558 for the sensor cable 440. In an embodiment, the attachment assembly 550 is a generally elongated, planar member having a top side 551, a bottom side 552, a first wing 554, a center 555 and a second wing 556. A button 559 mechanically couples the acoustic assembly 510 to the attachment assembly center 555 so that the acoustic assembly 510 extends from the bottom side 552.

Also shown in FIG. 5B, the optic assembly 530 is disposed on the attachment assembly bottom side 552 at the first wing 554. In other embodiments, the optic assembly 530 is disposed on the second wing 556 or both wings 554, 556. The interconnect assembly 540 routes along the bottom side 552 (as shown) or otherwise within and/or upon the attachment assembly 550 so as interconnect the acoustic 510 and optical 530 assemblies. The sensor cable 440 extends from one end of the interconnect 540 and attachment assemblies 550 to a sensor connector 450 (FIGS. 4A-B) at an opposite end so as to provide communications between the sensor 500 and a monitor 1000 (FIG. 1A), as described in further detail with respect to FIG. 9B, below. In an embodiment, the wings 554, 556 have an adhesive along the bottom side 552 so as to secure the acoustic 510 and optic 530 assemblies to a patient's skin, such as at a neck site 7 (FIG. 4A). A removable backing can be provided with the adhesive to protect the adhesive surface prior to affixing to a patient's skin. In other embodiments, the attachment assembly 550 has a circular or rounded shape, which advantageously allows uniform adhesion of the sensor head 500 to a measurement site. In a resposable embodiment, the attachment assembly 550 or portions thereof are removably attachable/detachable to the acoustic assembly 510, the optic assembly 530 or both and disposed. The acoustic 510 and/or optic 530 assemblies are reusable accordingly.

Figure 6A:
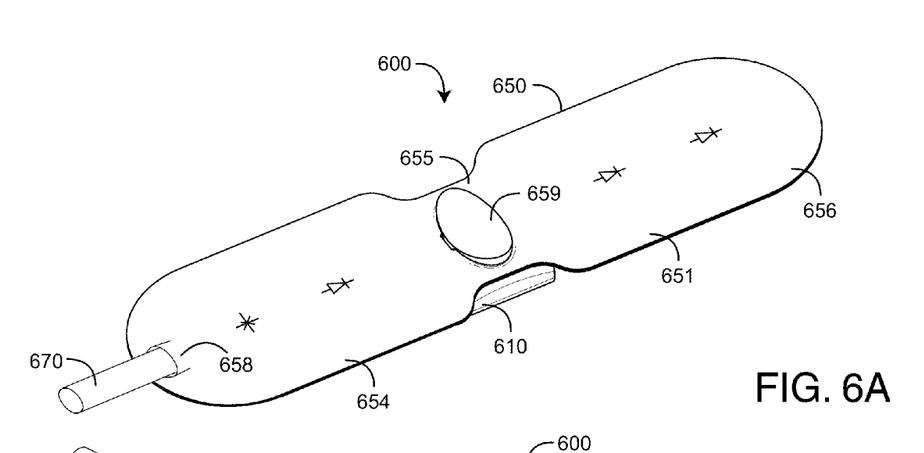
FIGS. 6A-B are detailed top and bottom perspective views, respectively, of a tissue-profile opticoustic sensor head.
Figure 6B:
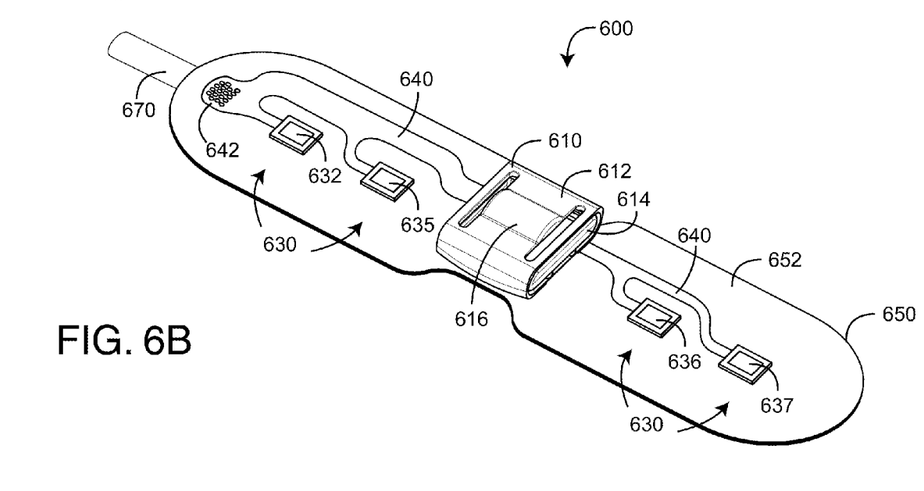

FIGS. 6A-B illustrates a tissue-profile sensor head 600 having acoustic 610, optic 630, interconnect 640 and attachment 650 assemblies and a sensor cable 670. The acoustic assembly 610 is as described above with respect to 510 (FIGS. 5A-B). The optic assembly 630 has an emitter subassembly 632 and multiple detector subassemblies 635-637. The emitter subassembly 632 and each of the detector subassemblies 635-637 are as described above with respect 532, 534 (FIG. 5B).

Advantageously, the optic assembly 630 is configured so that light transmitted from the emitter subassembly 632 passes into patient tissue and is reflected back to the detector subassemblies 635-637 after attenuation by pulsatile blood flow. Further, the tissue-attenuated light detected varies according to tissue depth and the spacing between the emitter subassembly 632 and a particular one of the detector subassemblies 635-637. Accordingly, the multiple detector subassemblies advantageously provide a tissue profile of $SpO_2$ versus depth. Specifically, simultaneous $SpO_2$ measurements are made at various tissue depths so as to distinguish blood-perfused surface tissue measurements from deeper tissues, veins and arteries.

As shown in FIGS. 6A-B, the acoustic assembly 610 and optic assembly 630 communicate with the sensor cable 670 via the interconnect assembly 640. In an embodiment, the interconnect assembly 640 is a flex circuit having multiple conductors that is adhesively bonded to the attachment assembly 650. The interconnect assembly 640 has a solder pad 642 or other interconnect to interface with the sensor cable 670, and the attachment assembly 650 has a molded strain relief 658 for the sensor cable 670. In an embodiment, the attachment assembly 650 is a generally elongated, planar member having a top side 651, a bottom side 652, a first wing 654, a center 655 and a second wing 656. A button 659 mechanically couples the acoustic assembly 610 to the attachment assembly center 655 so that the acoustic assembly 610 extends from the bottom side 652.

Also shown in FIGS. 6A-B, the optic assembly 630 is disposed on the attachment assembly bottom side 652 along the first wing 654 and second wing 656. The interconnect assembly 640 routes along the bottom side 652 (as shown) or otherwise within and/or upon the attachment assembly 650 so as interconnect the acoustic 610 and optical 630 assemblies. The sensor cable 670 extends from one end 642 of the interconnect assembly 640 and the attachment assembly 650 to a sensor connector 450 (FIGS. 4A-B) at an opposite end so as to provide communications between the sensor 600 and a monitor 1000 (FIG. 1A). The attachment assembly 650 is as described in detail above with respect to 550 (FIGS. 5A-B).

An advantageous application of a tissue-profile sensor head 600 is placement on a neck site 7 (FIG. 4A) so as to measure respiration parameters based upon tracheal airflow sounds, such as respiration rate, and so as to measure blood-related parameters based upon pulsatile blood flow within peripheral (surface) tissues, within the common carotid artery (CCA) and/or the jugular vein (JV), such as pulse rate and $SpO_2$. The CCA and JV are close to the neck skin surface and large in size, so as to facilitate optical reflectance measurements. Further, the CCA and JV supply and extract most of the blood to and from the brain and can therefore yield information regarding cerebral oxygen demand and corresponding metabolic rate parameters.

In a further advantageous embodiment of a tissue-profile sensor head 600, the acoustic assembly 610 and, in particular, the piezoelectric transducer subassembly or subassemblies thereof is configured to generate an active pulse into the tissue site so as to measure venous oxygen saturation ($SpvO_2$) and other blood constituents of the peripheral neck tissues. The use of an active pulse for blood constituent measurements is described in U.S. Pat. No. 5,638,816 titled Active Pulse Blood Constituent Monitoring, filed Jun. 7, 1995; and U.S. Pat. No. 6,334,065 titled Stereo Pulse Oximeter, filed May 27, 1999, both patents assigned to Masimo and both incorporated by reference herein. Transmitting acoustic vibrations into a tissue measurement site with an acoustic sensor and, in particular, the piezoelectric acoustic sensing element thereof by applying a relatively high voltage driver to the piezoelectric element is describe in U.S. patent application Ser. No. 12/904,789 titled Acoustic Respiratory Monitoring Systems and Methods, cited above.

In a particularly advantageous embodiment, an opticoustic sensor such as a tissue-profile sensor head 600 described above, when placed on the neck, has one or more acoustic sensor assemblies for measuring respiration rate acoustically (RRa) and one or more optical sensor assemblies for measuring respiration rate optically (RRo) so as to provide a more accurate measure of respiration rate; and the same optical sensor assemblies for measuring carotid artery $SpO_2$, jugular vein $SpO_2$, and peripheral tissue $SpO_2$; and a combination of the same acoustic and optical sensor assemblies for measuring peripheral tissue venous oxygen saturation SpvO2. Similar advantageous combined use of the acoustic and optical sensor assemblies of an opticoustic sensor may be obtained by attaching the tissue-profile sensor head 600, singularly or in multiple combinations of sensor heads, on various tissue sites of the body.

Another advantageous application of a tissue-profile sensor head 600 is placement on a forehead site 3 (FIG. 4B) so as to provide respiration parameters based upon paranasal sinus ostium airflow, turbulence and echoes and, further, cerebral oxygen saturation based upon pulsatile flow in blood-perfused brain tissues at various depths. Attached to a back or chest site, a tissue profile sensor head 600 provides respiration parameters based upon turbulent airflow in the lungs and various airways along with neonatal core oxygen saturation.

Figure 8:
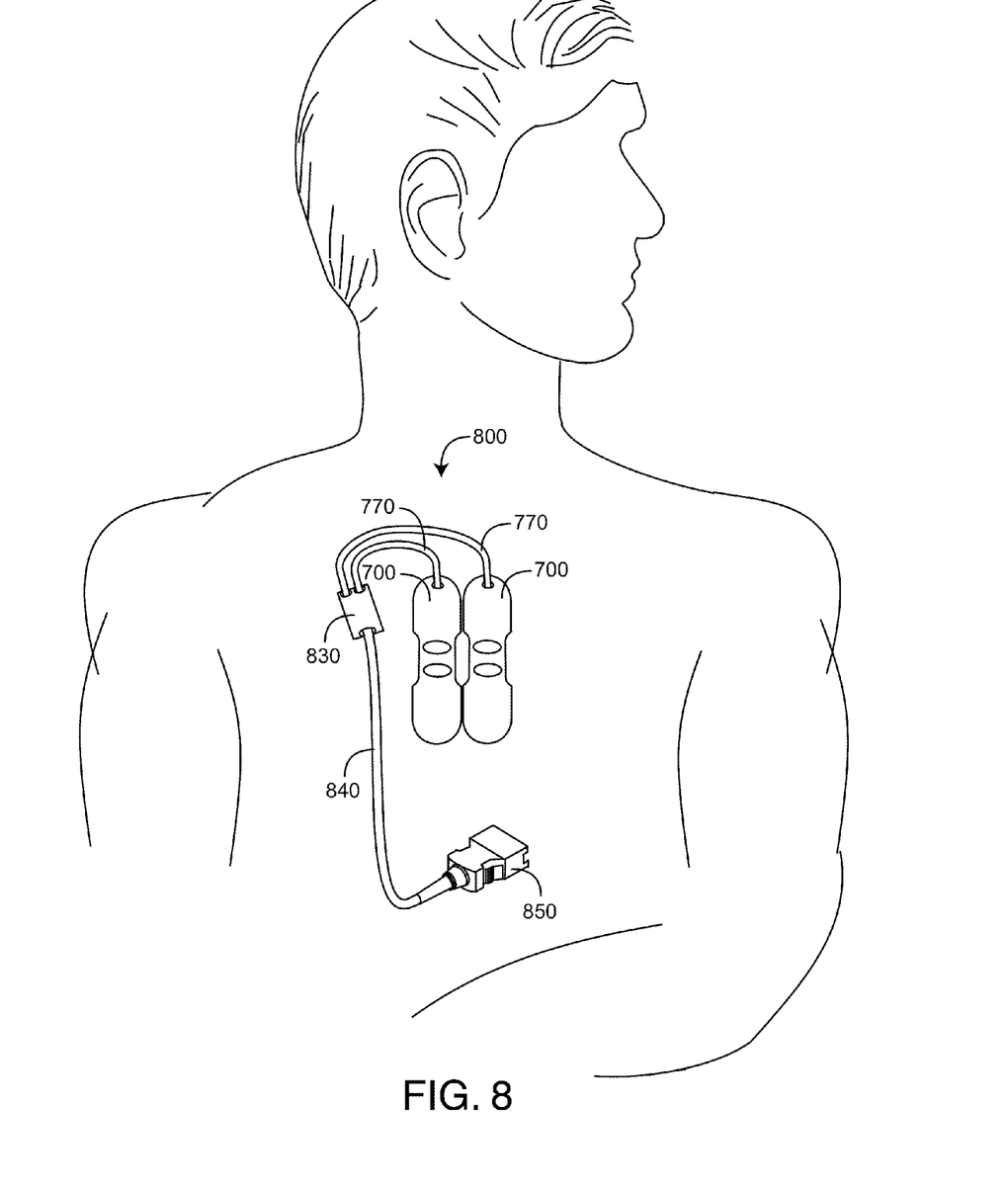
FIG. 8 is an illustration of an arrayed acoustic sensor embodiment.

In addition, a dual-head sensor, such as described with respect to FIG. 8, below, allows placement of one sensor head 600 at a neck site 7 (FIG. 4A) and another sensor head 600 at a forehead site 3 (FIG. 4B) so as to provide simultaneous oxygen saturation measurements of the CCA, brain tissue at various depths and the JV. Such simultaneous measurements provide an overall functional analysis of cerebral oxygen supply and metabolism along with a comprehensive diagnostic tool for cerebral injury and disease.

Figures 7A, 7B:
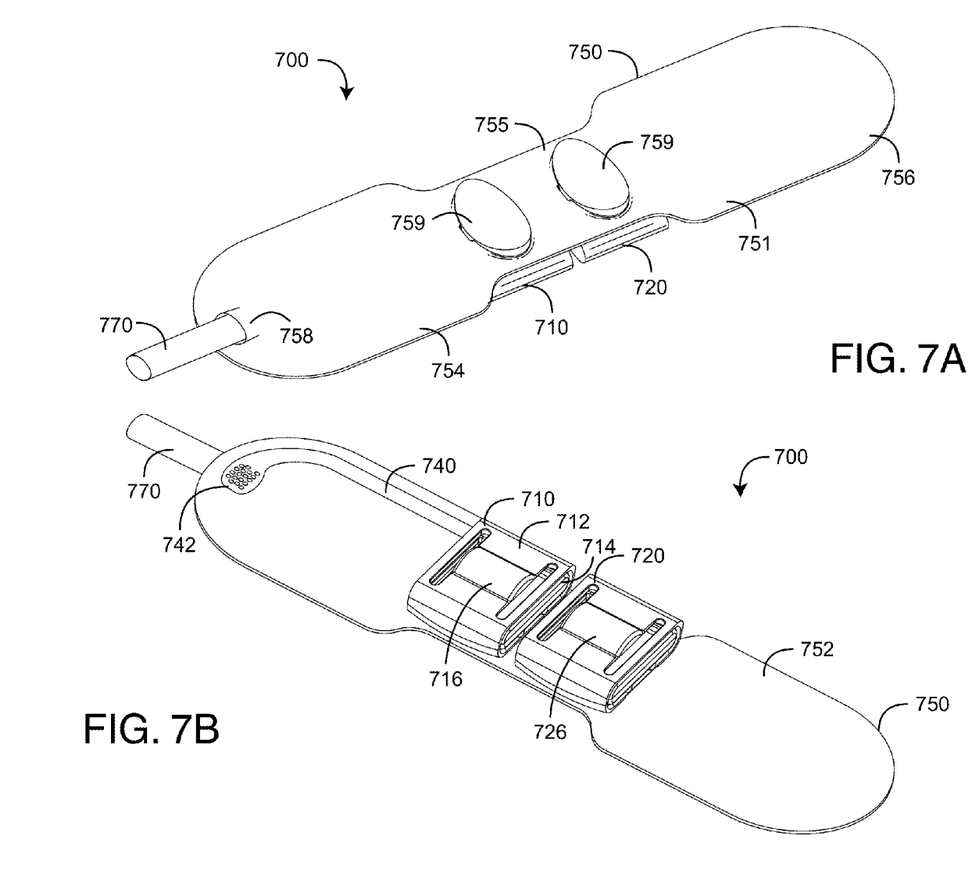
FIGS. 7A-B are detailed top and bottom perspective views, respectively, of a multiple-acoustic sensor head.

FIGS. 7A-B illustrate a multiple-acoustic sensor head 700 having a first acoustic assembly 710, a second acoustic assembly 720, an interconnect assembly 740, attachment assembly 750 and a sensor cable 770. Each acoustic assembly 710, 720 has an acoustic coupler 712 and a piezoelectric subassembly 714 including contact portions 716, 726 as described with respect to FIGS. 5A-B, above. The acoustic assemblies 710, 720 communicate with the sensor cable 770 via the interconnect assembly 740. In an embodiment, the interconnect assembly 740 is a flex circuit having multiple conductors that is adhesively bonded to the attachment assembly 750. The interconnect assembly 740 has a solder pad 742 or other interconnect so as to interface with the sensor cable 770, and the attachment assembly 750 has a molded strain relief 758 for the sensor cable 770. The attachment assembly 750 is a generally elongated, planar member having a top side 751, a bottom side 752, a first wing 754, a center 755 and a second wing 756. Buttons 759 mechanically couple the acoustic assemblies 710, 720 to the attachment assembly center 755 so that the acoustic assemblies 710, 720 extend from the bottom side 752. In an embodiment, the sensor head 700 may have an optical assembly such as described with respect to FIGS. 5A-B or FIGS. 6A-B, above.

In an advantageous embodiment, one of the acoustic assemblies 710, 720 is optimized for measuring pulse rate and heart sounds from the heart and the other one of the acoustic assemblies 710, 720 is optimized for separately measuring turbulent air sounds from the lungs and various airways. Heart sounds typically range in frequency from about 15 Hz-400 Hz and are relatively narrow band. By contrast, lung sounds typically range from about 600 Hz-2000 Hz and resemble broadband white-noise. Accordingly, in one embodiment, one of the piezo circuits 982 (FIG. 9B) of the acoustic assemblies 710, 720 is optimized for heart sounds and the other one of the piezo circuits 982 (FIG. 9B) is optimized for lung sounds.

An opticoustic sensor head 700 may be applied singly to a neck site, as described with respect to FIG. 1B, above, or to other sites including the chest or back. Further, multiple identical sensor heads 700 may be used in combination with a common cable in an arrayed sensor head embodiment, as described with respect to FIG. 8, below FIG. 8 illustrates an arrayed acoustic sensor 800 embodiment that advantageously accesses the spatial information contained in thoracic sounds. The arrayed acoustic sensor 800 has two or more multiple-acoustic sensor heads 700, head cables 770, a cable junction 830, a sensor cable 840 and a sensor connector 850. Each of the sensor heads 700 have multiple acoustic transducers, as described with respect to FIGS. 7A-B, above. The arrayed acoustic sensor 800 is responsive to both the direction and timing of body sounds. Such a configuration allows a continuous visualization of breath sound information during a complete breathing cycle, details regarding breath sound timing between the different lung locations and a quantification of the regional distribution of breath sounds. Although described with respect to FIGS. 7A-B, above, as having two acoustic transducers in each sensor head 700, an arrayed acoustic sensor 800 may have three or more acoustic transducers in each sensor head. Further, there may be three or more sensor heads 700 merged via the cable junction 830 into the sensor cable 840. In addition, two or more heads may be merged onto a single attachment assembly having sufficient size for both rows and columns of acoustic transducers. The merged assembly shares a single sensor cable 840, which eliminates the sensor junction 830. The arrayed acoustic sensor 800 may be attached at various neck, chest and back sites. Further, multiple arrayed opticoustic sensors 800 may be attached at multiple sites, such as chest, neck and back areas, and routed to a single monitor for analysis.

Figure 9A:
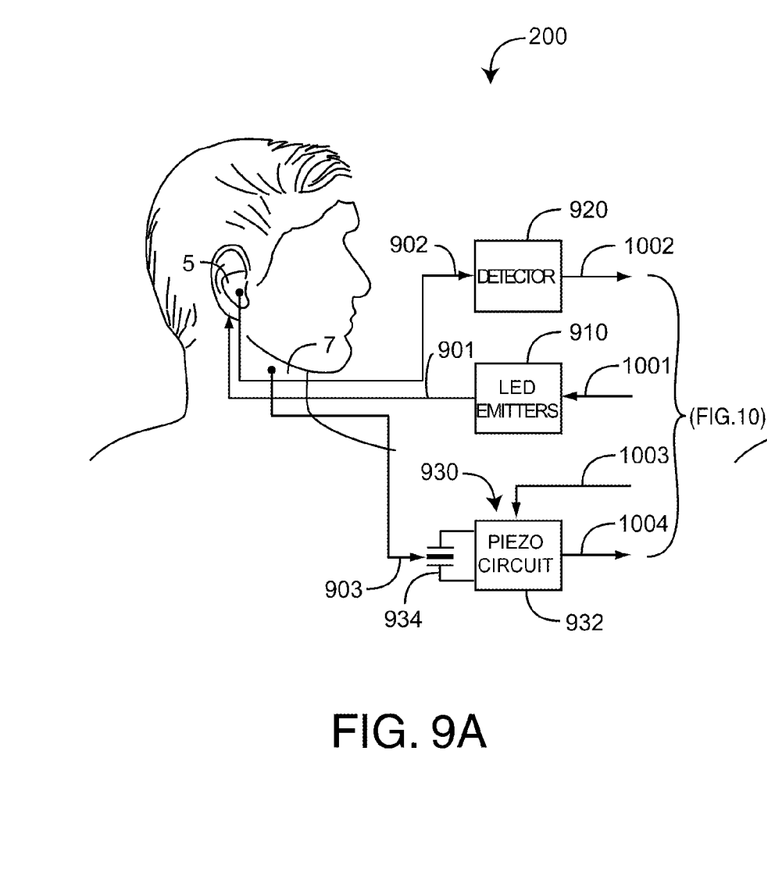
FIGS. 9A-B are detailed opticoustic sensor block diagrams.

FIG. 9A illustrates an opticoustic sensor 200 embodiment according to FIGS. 2-3 having an optic head 210 (FIG. 2) and an acoustic head 220 (FIG. 2). The optic head 210 (FIG. 2) has LED emitters 910 attached on one side of an ear concha site 5 and at least one detector 920 attached on the opposite side of the concha site 5. In an embodiment, the emitters 910 emit light 901 having at least one red wavelength and at least one IR wavelength, so as to determine a ratio of oxyhemoglobin and deoxygemoglobin in the pulsatile blood perfused tissues of the concha. In other embodiments, the emitters 910 generate light having more than two discrete wavelengths so as to resolve other hemoglobin components. Emitter drivers in the monitor 1000 (FIG. 10) activate the emitters 910 via drive lines 1001 in the sensor cables 110 (FIGS. 1A-B). The detector 920 generates a current responsive to the intensity of the received light 902 from the emitters 910 after attenuation by the pulsatile blood perfused concha tissue 5. One or more detector lines 1002 in the sensor cables 110 (FIGS. 1A-B) transmit the detector current to the monitor 1000 (FIG. 10) for signal conditioning and processing, as described with respect to FIG. 10, below.

Also shown in FIG. 9A, the acoustic head 220 (FIG. 2) has an acoustic sensor 930 attached to a neck site 7. The acoustic sensor 930 has a power interface 1003, a piezo circuit 932 and a piezoelectric element 934. The piezoelectric element 934 senses vibrations and generates a voltage in response to the vibrations, as described with respect to the various sensor embodiments, above. The signal generated by the piezoelectric element 934 is communicated to the piezo circuit 932, described immediately below, and transmits the signal 1004 to the monitor 1000 (FIG. 10) for signal conditioning and processing.

The piezo circuit 932 decouples the power supply and performs preliminary signal conditioning. In an embodiment, the piezo circuit 932 includes clamping diodes to provide electrostatic discharge (ESD) protection and a mid-level voltage DC offset for the piezoelectric signal to ride on, to be superimposed on or to be added to. The piezo circuit 932 may also have a high pass filter to eliminate unwanted low frequencies such as below about 100 Hz for breath sound applications, and an op amp to provide gain to the piezoelectric signal. The piezo circuit 932 may also have a low pass filter on the output of the op amp to filter out unwanted high frequencies. In an embodiment, a high pass filter is also provided on the output in addition to or instead of the low pass filter. The piezo circuit 932 may also provide impedance compensation to the piezoelectric element 934, such as a series/parallel combination used to control the signal level strength and frequency of interest that is input to the op amp. In one embodiment, the impedance compensation is used to minimize the variation of the piezoelectric element output. The impedance compensation can be constructed of any combination of resistive, capacitive and inductive elements, such as RC or RLC circuits.

Figure 9B:
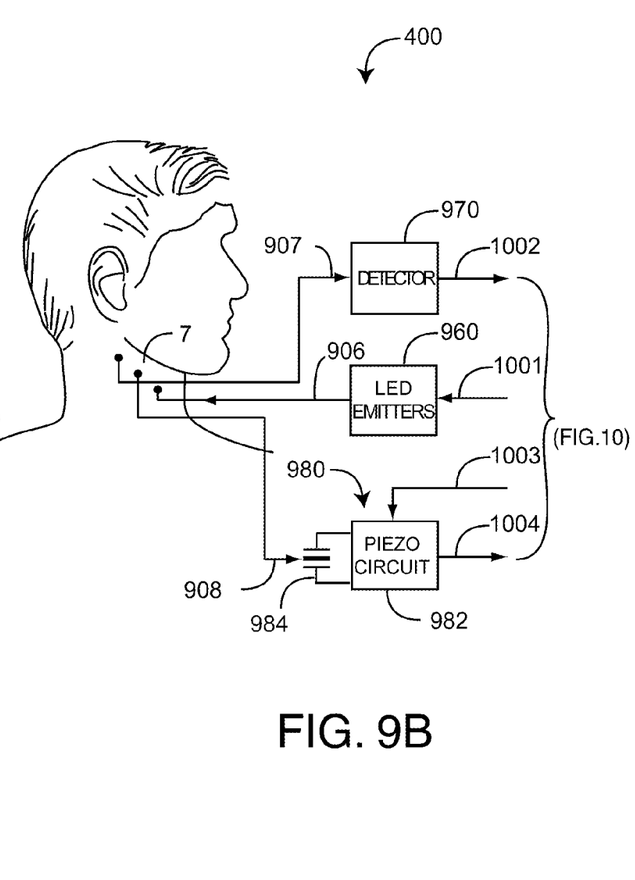

FIG. 9B illustrates an opticoustic sensor 400 embodiment according to FIGS. 4-5 having an integrated sensor with both optic and acoustic assemblies that attach along a neck site 7, as but one example. The optic assembly has LED emitters 960 and at least one detector 970 spaced apart at a predetermined distance. In an embodiment, the LEDs 960 emit light 906 having at least one red wavelength and at least one IR wavelength, so as to determine a ratio of oxyhemoglobin and deoxygemoglobin in pulsatile blood perfused tissue. In other embodiments, the LEDs 960 generate light having more than two discrete wavelengths so as to resolve other hemoglobin components. Emitter drivers in the monitor 1000 (FIG. 10) activate the emitters 960 via drive lines 1001 in the sensor and patient cables. The detector 970 generates a current responsive to the intensity of the received light 907 from the emitters 960 after reflection/attenuation by pulsatile blood perfused tissue. One or more detector lines 1002 transmit the detector current to the monitor 1000 (FIG. 10) for signal conditioning and processing, as described with respect to FIG. 10, below. Also shown in FIG. 9B, the acoustic assembly has an acoustic sensor 980 attached to, as but one example, a neck site 7. The acoustic sensor 980 has a power interface 1003, a piezo circuit 982 and a piezoelectric element 984, as described above with respect to FIG. 9A.

In multiple acoustic transducer embodiments, the piezo circuit 982 for one transducer is optimized for pulse and heart sounds and the piezo circuit 982 for another transducer is optimized for lung sounds. In an embodiment, a piezo circuit filter is relatively broadband and has a relatively high center frequency for lung/breath sounds and is relatively narrow band with a relatively low center frequency for pulse and heart sounds. In a particularly advantageous embodiment, acoustic-derived pulse and heart sounds are used to verify an optically-derived pulse rate as well as characteristics of plethysmograph waveforms.

Figure 10:
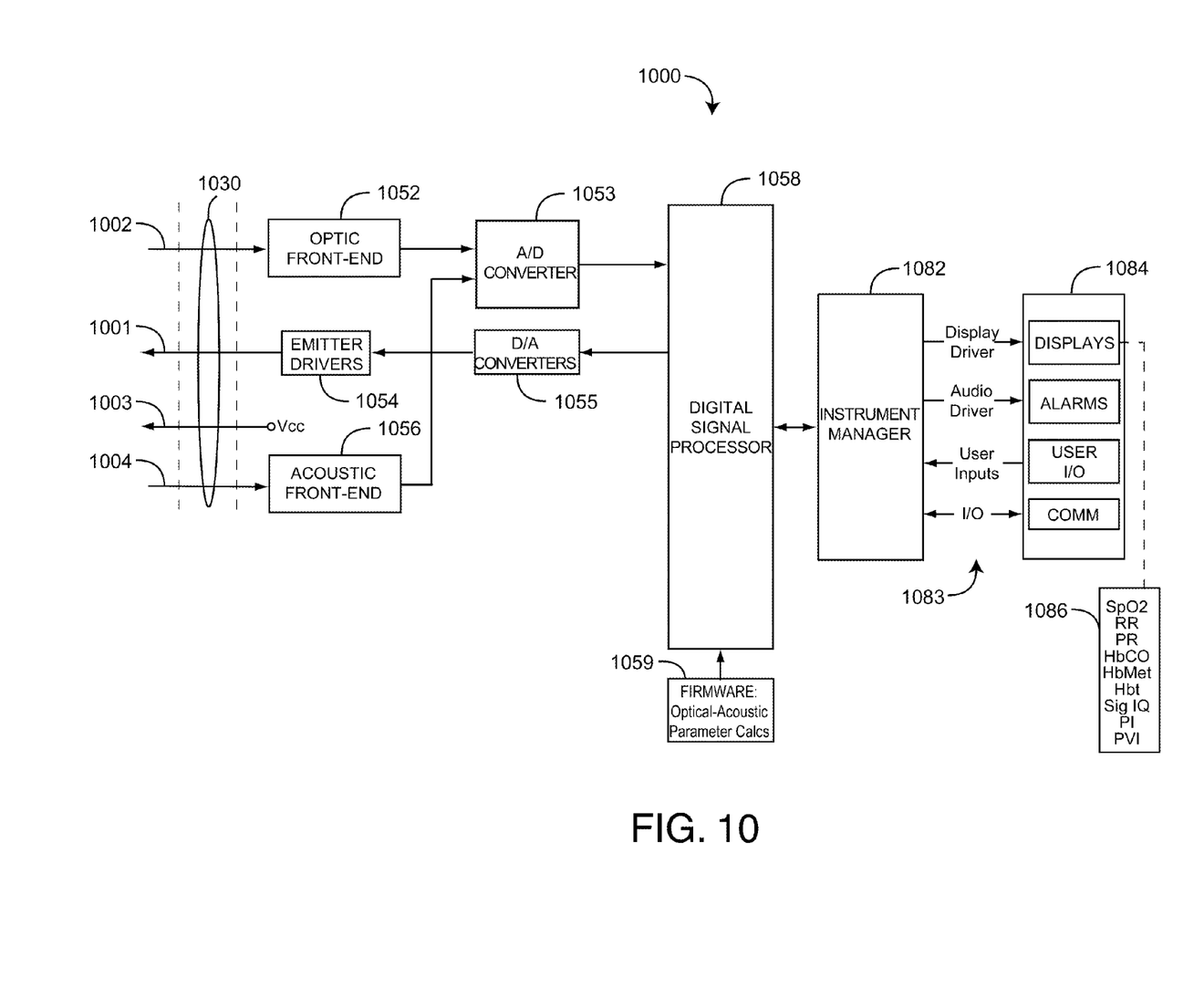
FIG. 10 is a detailed opticoustic monitor block diagram.

FIG. 10 illustrates a monitor 1000 for driving and processing signals from an opticoustic sensor 200, 400 (FIGS. 9A-B). The monitor 1000 includes an optical front-end 1052, an acoustic front-end 1056, an analog-to-digital (A/D) converter 1053, a digital signal processor (DSP) 1058, emitter drivers 1054 and digital-to-analog (D/A) converters 1055. In general, the D/A converters 1055 and drivers 1054 convert digital control signals into analog drive signals 1001 capable of activating the emitters 910, 960 (FIGS. 9A-B) via a sensor cable 1030. The optical front-end 1052 and A/D converter 1053 transform composite analog intensity signal(s) from light sensitive detector(s) received via the sensor cable 1030 into digital data input to the DSP 1058. The acoustic front-end 1056 and A/D converter 1053 transform analog acoustic signals from a piezoelectric element into digital data input to the DSP 1058. The A/D converter 1053 is shown as having a two-channel analog input and a multiplexed digital output to the DSP 1058. In another embodiment, each front-end 1052, 1056 communicates with a dedicated single channel A/D converter generating two independent digital outputs to the DSP 1058.

According to an embodiment, the DSP 1058 comprises a processing device based on the Super Harvard ARChitecture ("SHARC"), such as those commercially available from Analog Devices. However, the DSP 1058 can comprise a wide variety of data and/or signal processors capable of executing programs 1059 for determining physiological parameters from input data.

Also shown in FIG. 10, an instrument manager 1082 communicates with the DSP 1058 to receive physiological parameter information derived by the DSP firmware 1059. One or more I/O devices 1084 have communications 1083 with the instrument manager 1082 including displays, alarms, user I/O and instrument communication ports. The alarms may be audible or visual indicators or both. The user I/O may be, as examples, keypads, touch screens, pointing devices or voice recognition devices, to name a few. The displays may be indicators, numerics or graphics for displaying one or more of various physiological parameters 1086. The instrument manager 1082 may also be capable of storing or displaying historical or trending data related to one or more of the measured values or combinations of the measured values. A patient monitor is disclosed in U.S. application Ser. No. 11/367,033, filed on Mar. 1, 2006, titled Noninvasive Multi-Parameter Patient Monitor, which is assigned to Masimo and incorporated by reference herein.

In various embodiments, the monitor 1000 may be one or more processor boards installed within and communicating with a host instrument. Generally, a processor board incorporates the front-end 1052, 1056, drivers 1054, converters 1053, 1055 and DSP 1058. Accordingly, the processor board derives physiological parameters and communicates values for those parameters to the host instrument. Correspondingly, the host instrument incorporates the instrument manager 1082 and I/O devices 1084. A processor board may also have one or more microcontrollers (not shown) for board management, including, for example, communications of calculated parameter data and the like to the host instrument.

An opticoustic sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological sensor comprising:
   an optic assembly having an optic transducer;
   an acoustic assembly having an acoustic transducer, a piezoelectric subassembly having a piezoelectric membrane that moves on a frame in response to acoustic vibrations, and an acoustic coupler generally enveloping the piezoelectric subassembly;
   an attachment assembly having a bottom side having an adhesive for skin attachment, a top side, and a flexible body including a center and wings and supporting the acoustic assembly on the center of the flexible body and the optic assembly on at least one of the wings of the flexible body, the flexible body configured to be affixed to a tissue site;
   the acoustic assembly having a button that mechanically couples the acoustic coupler generally centered on the attachment assembly so that the acoustic assembly extends from the attachment assembly bottom side;
   the optic assembly configured to transmit a plurality of wavelengths of light into the tissue site and detect the light after attenuation by pulsatile blood flow within the tissue site, the detected light usable to generate an optic signal;
   the acoustic transducer configured to respond to vibrations at the surface of the tissue site, the vibrations usable to generate an acoustic signal; and
   a sensor cable that transmits the optic signal and the acoustic signal, the sensor cable connectable to a monitor for use in calculating a plurality of physiological parameters.

2. The physiological sensor according to claim 1 wherein the optic assembly comprises:
   a plurality of emitters that transmit light having a plurality of wavelengths in response to drive currents received from the monitor via the sensor cable;
   a detector responsive to light from the emitters that is reflected from the tissue site after attenuation by pulsatile blood flow within the tissue site; and
   the emitters and detector attached on the attachment assembly bottom side.

3. The physiological sensor according to claim 1 further comprising an interconnect assembly disposed along the attachment assembly bottom side so as to electrically connect the optic assembly and the acoustic assembly with the sensor cable.

4. The physiological sensor according to claim 3 wherein:
   the interconnect assembly is an elongated flex circuit having a plurality of conductors; and
   the sensor cable is electrically and mechanically mated with the interconnect assembly so that the sensor cable extends from an attachment assembly end.

5. The physiological sensor according to claim 1 further comprising a sensor cable anchor adapted to be adhesively attached proximate the tissue site in order to stabilize the sensor cable.

6. The physiological sensor according to claim 1 wherein the acoustic transducer is configured to transmit acoustic vibrations into the tissue site in order to provide an active pulse for optical assembly measurements of pulsed, blood perfused tissue.

* * * * *